United States Patent [19]

Margolin et al.

[11] Patent Number: 4,970,317

[45] Date of Patent: Nov. 13, 1990

[54] PROCESS FOR THE PREPARATION OF CASTANOSPERMINE ESTERS

[75] Inventors: Alexey L. Margolin, Fishers; Deborah L. Delinck, Indianapolis, both of Ind.

[73] Assignee: Merrell Dow Pharmaceuticals Inc., Cincinnati, Ohio

[21] Appl. No.: 390,794

[22] Filed: Aug. 8, 1989

[51] Int. Cl.$^5$ ............................................. C07D 221/02
[52] U.S. Cl. ................................................... 546/112
[58] Field of Search ........................................ 546/112

[56] References Cited

PUBLICATIONS

M. Therisod et al., *J. Am. Chem. Soc.*, 108, 5638 (1986).
H. M. Sweers et al., *J. Am. Chem. Soc.*, 108, 6421 (1986).
M. Therisod et al., *J. Am. Chem. Soc.*, 109, 3977 (1987).
S. Riva et al., *J. Am. Chem. Soc.*, 110, 584 (1988).
S. Riva et al., *J. Am. Chem. Soc.*, 110, 3291 (1988).
W. J. Hennen et al., *J. Org. Chem.*, 53, 4939 (1988).
F. Nicotra et al., *Tet. Letters*, 30, 1703 (1989).
F. Bjorkling et al., *J. Chem. Soc., Chem. Commun.*, 1989, 934.

*Primary Examiner*—Mary C. Lee
*Assistant Examiner*—Robert C. Whittenbaugh
*Attorney, Agent, or Firm*—John J. Kolano

[57] ABSTRACT

1-Esters of castanospermine have been prepared enzymatically from appropriate activated esters using substilisin. The esters obtained in this way can be further reacted enzymatically to give diesters which can, in turn, be selectively hydrolyzed to give monoesters in good yield.

6 Claims, No Drawings

PROCESS FOR THE PREPARATION OF CASTANOSPERMINE ESTERS

BACKGROUND OF THE INVENTION

Castanospermine is an alkaloid which has been isolated from the seeds of Castanospermum australe and it has the following formula:

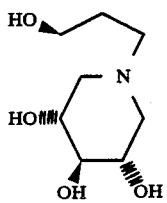

Systematically, this compound can be named in several ways as follows: [1S-(1α,6β,7α,8aβ)]-octahydro-1,6,7,8-indolizinetetrol or (1S,6S,7R,8R,8aR)-1,6,7,8-tetrahydroxyindolizidine or 1,2,4,8-tetradeoxy-1,4,8-nitrilo-L-glycero-D-galacto-octitol. The term "castanospermine" or the first systematic name will be used in the discussion below.

Esters of castanospermine and their activity as inhibitors of intestinal sucrase and lysosomal glucosidase and their utility in the treatment of diabetes has been described in European Patent Application No. 0 297 534. The indicated patent application describes the preparation of these esters but the procedures involved either give a mixture of esters which must be separated or involve multistep chemical synthesis.

DESCRIPTION OF THE INVENTION

The present invention is directed to a new enzymatic process for the preparation of esters of castanospermine. More particularly, it is directed to an enzymatic esterification process which selectively gives 1-esters of castanospermine. Thus, the present invention is directed to a process for the preparation of compounds having the following general formula:

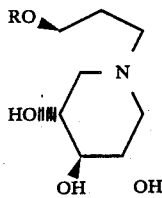

wherein R is $C_{1-10}$ alkanoyl, cyclohexanecarbonyl,

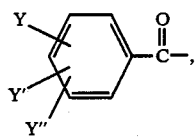

naphthalenecarbonyl optionally substituted by methyl or halogen, phenyl($C_{2-6}$ alkanoyl) wherein the phenyl is optionally substituted by methyl or halogen; pyridinecarbonyl optionally substituted by methyl or halogen; thiophenecarbonyl optionally substituted by methyl; furancarbonyl optionally substituted by methyl; Y is hydrogen, $C_{1-4}$ alkyl, $C_{1-4}$ alkoxy, halogen, trifluoromethyl, or $C_{1-4}$ alkylsulfonyl; Y' is hydrogen, $C_{1-4}$ alkyl, $C_{1-4}$ alkoxy, halogen or it is combined with Y to give 3,4-methylenedioxy; Y" is hydrogen, $C_{1-4}$ alkyl, $C_{1-4}$ alkoxy or halogen; which comprises reacting castanospermine with an ester of the formula

R'—C(O)—OR"

wherein R'—C(O)— is defined in the same way as R above and R" is vinyl or β-halogenated ethyl, with the reaction being carried out in a pyridine solvent in the presence of subtilisin.

The term "β-halogenated ethyl" used above indicates ethyl having from 1 to 3 fluorine or chlorine atoms on the carbon atom β to the free valence. Examples of such groups are 2,2,2-trichloroethyl, 2,2,2-trifluoroethyl, 2,2-dichloroethyl, 2,2-difluoroethyl, 2-chloroethyl and 2-fluoroethyl. Preferred groups for R" are vinyl 2,2,2-trichloroethyl or 2,2,2-trifluoroethyl. The term "pyridine solvent" is considered as encompassing pyridine itself and simple methylsubstituted pyridines such as α-picoline, β-picoline or γ-picoline. Pyridine is the preferred solvent for the reaction. The reaction is preferably carried out for 84 to 120 hours but, obviously, the reaction can be followed by thin layer chromatography to determine the extent to which reaction has taken place and the time period for the reaction can be modified accordingly. Obviously, shorter reaction times can be used although this may not provide the optimum yield of product. Alternatively, longer reaction times can also be used but, if the reaction is essentially complete earlier, there would be not advantage to using longer times.

The subtilisin enzyme used in the present process is a proteolytic enzyme isolated from strains of the soil bacteria Bacillus subtilis and this material is commercially available.

The $C_{1-10}$ alkanoyl groups referred to above can be straight- or branched-chain and can be exemplified by formyl, acetyl, propionyl, butyryl, isobutyryl, hexanoyl, octanoyl and decanoyl. The halogens referred to above can be exemplified by fluorine, chlorine, bromine or iodine. The $C_{1-4}$ alkyl groups referred to above, whether alone or as part of an alkoxy or an alkylsulfonyl or some other group, can be straight- or branched-chain alkyl groups containing up to 4 carbon atoms. Examples of various such groups are methyl, ethyl, propyl, butyl, methoxy, ethoxy, butoxy, methylsulfonyl or ethylsulfonyl. The phenyl($C_{2-6}$ alkanoyl) groups referred to above can be exemplified by benzeneacetyl and benzenepropionyl. The various naphthalenecarbonyl, pyridinecarbonyl, thiophenecarbonyl and furancarbonyl groups referred to above include the various position isomers and these can be exemplified by naphthalene-1-carbonyl, naphthalene-2-carbonyl, nicotinoyl, isonicotinoyl, thiophene-2-carbonyl, thiophene-3-carbonyl, furan-2-carbonyl and furan-3-carbonyl. The naphthalene, pyridine, thiophene and furan groups can be optionally further substituted as indicated above.

A preferred embodiment of the present invention is the use of the process to prepare those compounds in which R is $C_{1-10}$ alkanoyl.

The 1-esters of castanospermine as obtained by the process described above are themselves active and useful compounds or they can be used as intermediates in the preparation of diesters which are themselves useful or which can be selectively hydrolyzed to give other monoesters. Thus, in particular, the 1-esters of castanospermine as obtained by the procedure described above can be further enzymatically reacted with another molecule of an ester of the formula $$R'-C(O)-OR''$$

wherein R' and R" are defined as above to give a mixture of the corresponding 1,7- and 1,6-diesters of castanospermine with the 1,7-diesters being preferred. The reaction is carried out in the presence of a lipase enzyme in an inert solvent. Examples of useful inert solvents are tetrahydrofuran, t-amyl alcohol, acetonitrile or acetone with tetrahydrofuran being preferred. The lipase enzyme as used above can be obtained from different sources. Thus, for example, it is possible to use porcine pancreatic lipase (PPL) or lipase from *Chromobacterium viscosum* (CV). The 1,7-diesters thus obtained can be selectively hydrolyzed with subtilisin enzyme to give the corresponding 7-monoester.

The compounds obtained by the process of the present invention are useful in the treatment of diabetes. More specifically, they can be used to prevent the development of excessive hyperglycemia which may be observed in certain diabetic conditions when a glucose precursor is ingested. Thus, when carbohydrate is ingested either as glucose or in a form such as maltose, sucrose or starch in food or drink, the serum glucose level rises to elevated concentrations. In healthy subjects, this hyperglycemic state quickly returns to normal, the glucose in the blood being rapidly metabolized and stored and/or utilized by the organism. In diabetes mellitus, however, the glucose tolerance of the patient is lowered and the abnormally high serum glucose levels which develop remain elevated for prolonged periods of time. A similar response to that seen in man can also be observed in other animals, including livestock, poultry, pet animals and laboratory animals. Such a condition can be described as postprandial hyperglycemia. One method for treating such a condition would be by administration of some agents which would prevent the conversion of complex sugars to glucose and thus prevent the development of the excessive glucose levels. In the present invention, it has been found that, where the high levels of glucose are a result of the hydrolysis of complex sugars, administration of the present castanospermine derivatives inhibits the initial formation of glucose in the blood and thus makes it possible to avoid the problems which would be associated with prolonged high levels of serum glucose.

The mechanism whereby this result is achieved is the following although the utility described above should not be limited by the precise details of this mechanism. Enzymes which catalyze the hydrolysis of complex carbohydrates convert nonabsorbable carbohydrate into absorbable sugars. The rapid action of these enzymes lead to acute and undesirable elevations in serum glucose in diabetes. The compounds of the present invention are potent inhibitors of these enzymes and, when co-administered with carbohydrate meal they prevent harmful hyperglycemic excursions of this type. It is desirable, however, that the inhibition of these hydrolytic enzymes be selective for those present in the intestine and that is true for the present compounds. Otherwise, inhibition of systemic glycohydrolases may lead to difficulty in the utilization of intracellular carbohydrates. The first enzyme described above is intestinal sucrase whereas the second enzyme is intracellular lysosomal α-glucosidase. The compounds obtained by the process of the present invention are tested for activity against these enzymes by the following procedures.

Intestinal Sucrase

Sucrase is isolated from rat intestine as a crude homogenate using the salt extraction procedure of Kolinska [*Biochem. Biophys. Acta*, 284, 235 (1984)]. Incubation mixtures contained 100 μl of enzyme preparation plus test compound and are incubated for 1 hour before the addition of 6.6 μmole sucrose in 100 μl 0.1 M sodium maleate, pH 5.9. The mixtures are incubated an additional 30 minutes and then heat inactivated at 80°-100° C. for 3 minutes Denatured protein is removed by centrifugation. Glucose liberated is; determined by glucose dehydrogenase reagents (Seragen Diagnostics).

Lysosomal α-Glucosidase

Lysosomal α-glucosidase is isolated and partially purified from rat liver by the method of Dissous [*Anal. Biochem.*, 116, 35 (1981)] through the ammonium sulfate fractionation steps. Enzyme is incubated with test compound for 1 hour at 37° C. prior to the addition of p-nitrophenyl-α-D-glucoside in a final volume of 0.6 ml of 0.1M sodium acetate, 25 mM potassium chloride, pH 4.2. Mixtures are incubated for an additional 30 minutes at 37° C. and then heat inactivated at 90° C. Denatured protein is removed by centrifugation. One ml of 0.1M sodium carbonate is added to the supernatant fraction and liberated nitrophenol determined by its absorption at 410 nm.

The compounds obtained by the process of the present invention can be further tested in a sucrose load test to determine their ability to inhibit serum glucose elevation. The procedure can be summarized as follows.

ICR Swiss mice, fasted for overnight, are orally dosed with test compound plus sucrose at 2.0 g/kg. At 30 minutes post sucrose, the animals are sacrificed and their serum glucose concentrations were determined. The amount of test compound needed to significantly inhibit the serum glucose elevation is determined by comparison to the serum glucose concentration of animals dosed only with sucrose. To test duration of action, mice are orally dosed twice. The initial dose is test compound or vehicle. After 1, 2, or 3 hours, the mice are dosed with sucrose at 2.0 g/kg. After an additional 30 minutes post sucrose, the animals are sacrificed and their serum glucose concentrations are determined. Test compound activity is indicated by a significant difference of serum glucose concentration from the corresponding control.

Sprague Dawley rats, fasted overnight, are orally dosed with test compound plus sucrose at 2.0 g/kg. At times of 0, 0.5, 1.0, 1.5, 2.0, 2.5 and 3.0 hours post dose, plasma samples are analyzed for glucose concentration. To test duration of action, rats were orally dosed twice. The initial dose is water or test compound at an effective dose. After 1 or 4 hours, rats are dosed with sucrose at 2.0 g/kg. Plasma samples are taken at 0.5, 1.0, 1.5, 2.0, 2.5 and 3.0 hours and analyzed for glucose concentration. Test compound activity is indicated by a significant difference from the corresponding control using area-under-the curve.

The effective amount of the compound, that is, the amount sufficient to inhibit postprandial hyperglycemia, depends on various factors such as the size, type and age of the animal to be treated, the particular compound or pharmaceutically acceptable salt employed, the frequency of administration, the severity of the condition and the time of administration. Generally speaking, the compounds would be administered orally at a dose of 0.1 mpk to 50 mpk, with a dose of 0.5 mpk to 5 mpk being preferred. More specifically, the present compounds would be administered to humans in single unit doses containing 35 mg to 350 mg of active ingredient with the material being administered three times a day at mealtime.

In using the compounds obtained by the present process, the active ingredient is preferably incorporated in a composition comprising a pharmaceutical carrier and from about 5 to about 90 percent by weight of a compound of the invention or a pharmaceutically-acceptable salt thereof. The term "pharmaceutical carrier" refers to known pharmaceutical excipients useful in formulating pharmaceutically active compounds for internal administration to animals, and which are substantially non-toxic and non-sensitizing under conditions of use. The compositions can be prepared by known techniques for the preparation of tablets, capsules, elixirs, syrups, emulsions, dispersions and wettable and effervescent powders, and can contain suitable excipients known to be useful in the preparation of the particular type of composition desired. Suitable pharmaceutical carriers and formulation techniques are found in standard texts, such as *Remington's Pharmaceutical Sciences*, Mack Publishing Company, Easton, Pa.

The following examples are presented to illustrate the present invention. However, they should not be construed as limiting it in any way. The various esters used as starting materials in these examples are either commercially available, or known in the literature or they can be prepared by standard known procedures. Thus, for examples, the esters can be prepared from the appropriate alcohol by using the procedure described by Steglich et al., *Angew. Chem., Int. Ed. Engl.* 8, 981 (1969).

EXAMPLE 1

To a solution of 170 mg of castanospermine in 15 ml of warm anhydrous pyridine was added 396 mg of 2,2,2-trichloroethyl butyrate. Then, 75 mg of solid subtilisin was added. [Commercial subtilisin (EC 3.4.21.4, protease from *B. subtilis*) was dissolved in 0.1M phosphate buffer, pH 7.8, and was freeze-dried.] The resulting suspension was shaken at 45° C. and 260 rpm for four days during which time aliquots were withdrawn and analyzed by thin layer chromatography (8% ethanol in methylene chloride). The enzyme (subtilisin) was removed by filtration and the pyridine solvent was evaporated under reduced pressure. The residual material was purified by silica gel radial chromatography (8% ethanol in methylene chloride) to give [1S-(1α,6β,7α,8β,8aβ)]-octahydro-1,6,7,8-indolizinetetrol 1-butyrate in a yield of 82%.

Alternatively, instead of purifying the crude product obtained by chromatography, the residue obtained after filtration of the subtilisin and evaporation of the pyridine was simply recrystallized from warm ethyl acetate to give [1S-(1α,6β,7α,8aβ)]-octahydro-1,6,7,8-indolizinetetrol 1-butyrate as a white crystalline solid melting at about 150°-151° C. (69% yield).

EXAMPLE 2

When the procedure of the first paragraph of Example 1 was repeated using 2,2,2-trifluoroethyl octanoate in place of the 2,2,2-trichloroethyl butyrate, there was obtained [1S-(1α, 6β, 7α, 8β,8aβ)]-octahydro-1,6,7,8-indolizinetetrol 1-octanoate as a waxy yellow semisolid: $R_f$ 0.23 (8% ethanol in methylene chloride). MS: m/e 316 [MH+], m/e 298 [MH+-H_2O], m/e 172 [MH+—HOC(O)CH_2(CH_2)_5CH_3]. (yield, 23%)

The same general procedure was repeated using castanospermine and vinyl acetate (2.2 mmol) and a reaction time of 84 hours to give [1S-(1α, 6β,7α, 8β, 8aβ)]-octahydro-1,6,7,8-indolizinetetrol 1-acetate melting at about 151°-153° C. (yield, 91%)

Likewise, the reaction of castanospermine with vinyl phenylacetate for 96 hours gave [1S-(1α,6β,7α,8β,-8aβ)]-octahydro-1,6,7,8-indolizinetetrol 1-phenylacetate melting at about 110°-112° C. (yield, 30%)

EXAMPLE 3

When the procedure of the first paragraph of Example 1 is repeated using the appropriate ester of benzoic acid or a substituted benzoic acid, or the appropriate ester of cyclohexanecarboxylic acid, pyridinecarboxylic acid, thiophenecarboxylic acid or furancarboxylic acid, the corresponding 1-esters of castanospermine are obtained.

EXAMPLE 4

[1S-(1α,6β,7α,8β,8aβ)]-Octahydro-1,6,7,8-indolizinetetrol 1-phenylacetate (1.5 mmol) was dissolved in 15 ml of anhydrous tetrahydrofuran. Then, 4 molar equivalents of 2,2,2-trichloroethyl butyrate was added. Then, using the resulting solution, lipase CV (10 mg/ml, lipase from *Chromobaerium viscosum* was lyophilized from 0.1M phosphate buffer at pH 7.0 before use) was added and the suspension was shaken at 45° C. for three days. When the reaction leveled off as shown by thin layer chromatography, the enzyme was removed by filtration, the tetrahydrofuran was evaporated under reduced pressure, and the resulting residue was chromatographed using radial chromatograph in an ethanol/methylene chloride system. The product obtained in this way was [1S-(1α,6β,7α,8β,8aβ)]-octahydro-1,6,7,8-indolizinetetrol 1-phenylacetate 7-butyrate as an oil. MS: m/e 378 [MH+], m/e 360 [MH+-H_2O], m/e 290 [MH+-HO-C(O)CH_2CH_2CH_3], m/e 242 [MH+—HO—C(O)CH_2C_6H_5].

When the above procedure was repeated using [1S-(1α,6β, 7α,8β,8aβ)]-octahydro-1,6,7,8-indolizinetetrol 1-butyrate and 2,2,2-trichloroethyl butyrate, the product obtained was [1S-(1α,6β,7α,8β,8aβ)]-octahydro-1,6,7,8-indolizinetetrol 1,7-dibutyrate as an oil. MS: m/e 330 [MH+], m/e 312 [MH+-H_2O], m/e 242 [MH+-HOC(O)CH_2CH_2CH_3].

In a similar manner, the reaction of [1S-(1α,6β,7α,8β, 8aβ)]-octahydro-1,6,7,8-indolizinetetrol 1-acetate with 2,2,2-trichloroethyl butyrate gave [1S-(1α,6β,7α,8-β8aβ)]-octahydro-1,6,7,8-indolizinetetrol 1-acetate 7-butyrate as a waxy semisolid. MS: m/e 302 [MH+], m/e 284 [MH+-H_2O], m/e 242 [MH+-HOC(O)CH_3].

Additionally, the reaction of [1S-(1α, 6β, 7α, 8β8aβ)]-octahydro-1,6,7,8-indolizinetetrol 1-butyrate with vinyl phenylacetate in a similar manner gave [1S-(1β,6β,7α,8β,8aβ)]-octahydro-1,6,7,8-indolizinetetrol 1-butyrate 7phenylacetate as a waxy semisolid. MS: m/e 378 [MH+], m/e 360 [MH+-H_2O], m/e 290 [MH+-HOC(O)CH_2CH_2CH_3], m/e 242 [MH+HOC(O)CH_2C_6H_5].

EXAMPLE 5

A solution of 189 mg of [1S-(1α,6β,7α,8β,8aβ)]-octahydro-1,6,7,8-indolizinetetrol 1,7-dibutyrate in 57 ml of phosphate buffer (pH 6.0) containing 10% ethanol was prepared and subtilisin Carlsberg (5 mg/ml) was added. The reaction was followed by thin layer chromatography using 10% ethanol in methylene chloride to follow the reaction. After 7 hours, castanospermine started to appear and the reaction was stopped by freezing and the reaction mixture was lyophilized. The lyophilized powder was subjected to radial chromatography using a mixture of 8% ethanol in methylene chloride. The product obtained in 64% yield was [1S-(1α,6β,7α,8β,8aβ)]-octahydro-1,6,7,8-indolizinetetrol 7-butyrate.

If the procedures described above are repeated using the appropriate esters of benzoic acid, substituted benzoic acids or other acids within the scope of the present invention as set forth above, the corresponding esters of castanospermine are obtained.

Similarly, if the procedure of Example 1 is repeated using 2-chloroethyl butyrate or 2,2-dichloroethyl butyrate, the product obtained is [1S-(1α,6β,7α,8β8aβ)]-octahydro-1,6,7,8-indolizinetetrol 1-butyrate.

What is claimed is:

1. A process for the preparation of compounds of the formula

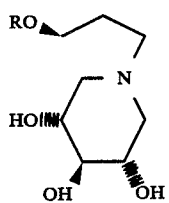

wherein R is $C_{1-10}$ alkanoyl, cyclohexanecarbonyl,

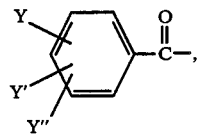

naphthalenecarbonyl optionally substituted by methyl or halogen, phenyl($C_{2-6}$ alkanoyl) wherein the phenyl is unsubstituted or substituted by methyl or halogen; pyridinecarbonyl optionally substituted by methyl or halogen; thiophenecarbonyl optionally substituted by methyl; furancarbonyl optionally substituted by methyl; Y is hydrogen, $C_{1-4}$ alkyl, $C_{1-4}$ alkoxy, halogen, trifluoromethyl, or $C_{1-4}$ alkylsulfonyl; Y' is hydrogen, $C_{1-4}$ alkyl, $C_{1-4}$ alkoxy, halogen or it is combined with Y to give 3,4-methylenedioxy; Y" is hydrogen, $C_{1-4}$ alkyl, $C_{1-4}$ alkoxy or halogen; which comprises reacting castanospermine with an ester of the formula

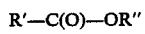

wherein R'—C(O)— is defined in the same way as R above and R" is vinyl or β-halogenated ethyl, with the reaction being carried out in a pyridine solvent in the presence of subtilisin.

2. A process according to claim 1 for the preparation of compounds of the formula:

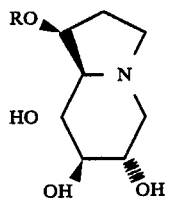

wherein R is $C_{1-10}$ alkanoyl, cyclohexanecarbonyl,

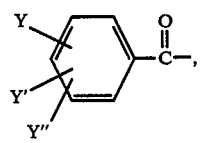

naphthalenecarbonyl optionally substituted by methyl or halogen, phenyl($C_{2-6}$ alkanoyl) wherein the phenyl is unsubstituted or substituted by methyl or halogen; pyridinecarbonyl optionally substituted by methyl or halogen; thiophenecarbonyl optionally substituted by methyl; furancarbonyl optionally substituted by methyl; Y is hydrogen, $C_{1-4}$ alkyl, $C_{1-4}$ alkoxy, halogen, trifluoromethyl, or $C_{1-4}$ alkylsulfonyl; Y' is hydrogen, $C_{1-4}$ alkyl, $C_{1-4}$ alkoxy, halogen or it is combined with Y to give, 3,4-methylenedioxy; Y" is hydrogen, $C_{1-4}$ alkyl, $C_{1-4}$ alkoxy or halogen; which comprises reacting castanospermine with an ester of the formula

wherein R'—C(O)— is defined in the same way as R above and R" is vinyl, 2,2,2-trichloroethyl or 2,2,2-trifluoroethyl, with the reaction being carried out in pyridine in the presence of subtilisin.

3. A process according to claim 1 for the preparation of compounds of the formula:

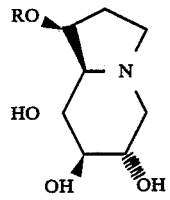

wherein R is $C_{1-10}$ alkanoyl, cyclohexanecarbonyl,

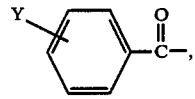

phenyl($C_{2-6}$ alkanoyl) wherein the phenyl is unsubstituted or substituted by methyl or halogen; Y is hydrogen, $C_{1-4}$ alkyl, $C_{1-4}$ alkoxy or halogen; which comprises reacting castanospermine with an ester of the formula

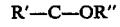

wherein R'—C(O)— is defined in the same way as R above and R" is vinyl, 2,2,2-trichloroethyl or 2,2,2-trifluoroethyl, with the reaction being carried out in pyridine in the presence of subtilisin.

4. A process according to claim 1 for the preparation of compounds of the formula:

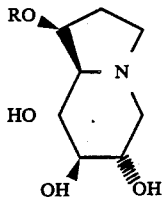

wherein R is C$_{1-10}$ alkanoyl; which comprises reacting castanospermine with an ester of the formula

R'—C(O)—RO'' wherein R'—C(O)— is defined in the same way as R above and R' is vinyl, 2,2,2-trichloroethyl or 2,2,2-trifluoroethyl, with the reaction being carried out in pyridine in the presence of subtilisin.

5. A process according to claim 1 for the preparation of [1S-(1α,6β,7α,8β,8aβ)]-octahydro-1,6,7,8-indolizinetetrol 1-butyrate which comprises reacting castanospermine with the vinyl, 2,2,2-trichloroethyl or 2,2,2-trifluoroethyl ester of butyric acid in pyridine in the presence of subtilisin.

6. A process according to claim 1 for the preparation of [1S-(1α,6β,7α,8β,8aβ)]-octahydro-1,6,7,8-indolizinetetrol 1-butyrate which comprises reacting castanospermine with the 2,2,2-trichloroethyl ester of butyric acid in pyridine in the presence of subtilisin.

* * * * *

UNITED STATES PATENT AND TRADEMARK OFFICE
CERTIFICATE OF CORRECTION

PATENT NO. : 4,970,317
DATED : November 13, 1990
INVENTOR(S) : Alexey L. Margolin, Deborah L. Delinck It is certified that error appears in the above-identified patent and that said Letters Patent is hereby corrected as shown below:

Column 1, Line 10, patent reads:

   should read   

Column 1, Line 20 patent reads: "7α,8aβ)]" and should read: --7α,8β,8aβ)]--.
Column 1, Line 45, patent reads:

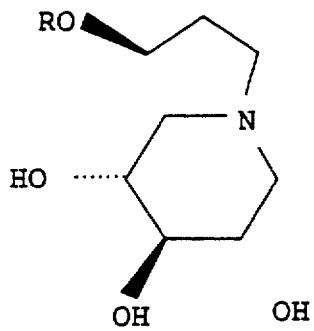   should read   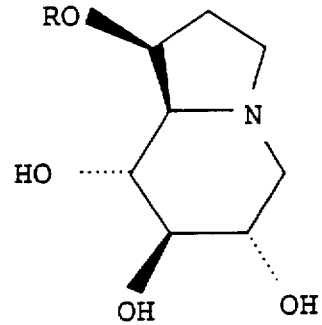

Column 3, Line 59, patent reads: "meal" and should read --meal,--.
Column 4, Line 13, patent reads: "is;" and should read --is--.
Column 5, Line 59, patent reads: "6β,7α,8aβ)]" and should read --6β,7α,8β,8aβ)]--.
Column 6, Line 29, patent reads: "Chromobaerium" and should read --Chromobacterium--.
Column 7, Line 30, patent reads:

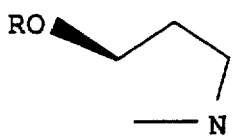   should read   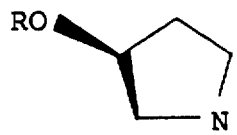

UNITED STATES PATENT AND TRADEMARK OFFICE
CERTIFICATE OF CORRECTION

PATENT NO. : 4,970,317

DATED : November 13, 1990

INVENTOR(S) : Alexey L. Margolin, Deborah L. Delinck

It is certified that error appears in the above-identified patent and that said Letters Patent are hereby corrected as shown below:

Column 8, Lines 5 and 45, and Column 9, line 10, patent reads:

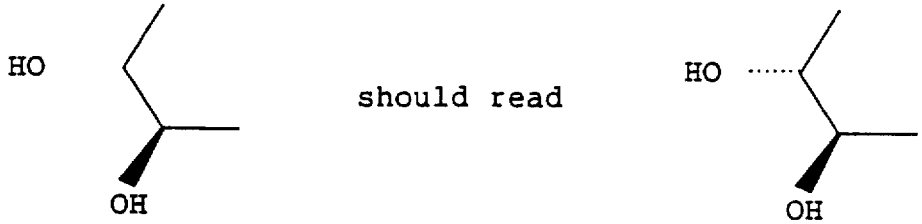

Column 10, Line 1, patent reads: "R'-C(O)-RO"" and should read -- R'-C(O)-OR"--.
Column 10, Line 4, patent reads: "R'" and should read --R"--.
Abstract, patent reads: "substilisin" and should read --subtilisin--.

Signed and Sealed this

Seventh Day of April, 1992

Attest:

HARRY F. MANBECK, JR.

Attesting Officer     Commissioner of Patents and Trademarks